United States Patent [19]

Nelson

[11] 4,176,236

[45] Nov. 27, 1979

[54] COMPOSITION AND PROCESS

[75] Inventor: Norman A. Nelson, Galesburg, Mich.

[73] Assignee: The Upjohn Company, Kalamazoo, Mich.

[21] Appl. No.: 784,995

[22] Filed: Apr. 6, 1977

Related U.S. Application Data

[62] Division of Ser. No. 647,369, Jan. 28, 1976, Pat. No. 4,032,576.

[51] Int. Cl.$^2$ .......................................... C07C 177/00
[52] U.S. Cl. ................................................. 568/838
[58] Field of Search ...................... 260/617 R; 568/838

[56] References Cited

U.S. PATENT DOCUMENTS

| | | | |
|---|---|---|---|
| 3,914,282 | 10/1975 | Pike | 560/121 |
| 3,932,463 | 1/1976 | Schaub et al. | 560/121 |
| 3,933,889 | 1/1976 | Magerlein | 560/121 |
| 3,959,346 | 5/1976 | Schneidner | 560/121 |
| 3,962,293 | 6/1976 | Magerlein | 560/121 |

OTHER PUBLICATIONS

Burger, "Medicinal Chemistry", pp. 81–82 (1960).
Derwent Farmdoc CPI No. 45723 v/25 (12-06-74).

*Primary Examiner*—Gerald A. Schwartz
*Attorney, Agent, or Firm*—Robert A. Armitage

[57] ABSTRACT

This invention comprises certain analogs of the prostaglandins in which the C-1 carboxyl is replaced by a primary alcohol. Also provided in this invention, are novel chemical processes useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

8 Claims, No Drawings

COMPOSITION AND PROCESS

The present application is a divisional application of Ser. No. 647,369 filed Jan. 28, 1976, now issued as U.S. Pat. No. 4,032,576 on June 28, 1977.

I claim:

1. A prostaglandin analog of the formula

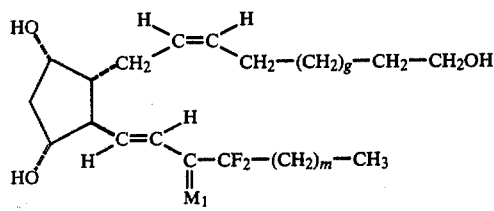

wherein $M_1$ is

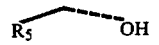

or

wherein $R_5$ is hydrogen or methyl;
wherein g is one, 2, or 3; and
wherein m is one to 5, inclusive.

2. A compound according to claim 1, wherein m is one or 2.

3. A compound according to claim 1, wherein m is 4 or 5.

4. A compound according to claim 1, wherein m is 3.

5. A compound according to claim 4, wherein g is one.

6. A compound according to claim 5, wherein $R_5$ is hydrogen.

7. 2-Decarboxy-2-hydroxymethyl-16,16-difluoro-$PGF_{2\alpha}$.

8. 2-Decarboxy-2-hydroxymethyl-15-methyl-$PGF_{2\alpha}$.

* * * * *

UNITED STATES PATENT OFFICE
CERTIFICATE OF CORRECTION

Patent No. 4,176,236   Dated  27 November 1979

Inventor(s) Norman A. Nelson

It is certified that error appears in the above-identified patent and that said Letters Patent are hereby corrected as shown below:

The Title should read -- 2-Decarboxy-2-Hydroxymethyl-$PGF_{2\alpha}$ Analogs --

Column 2, line 22, "2-Decarboxy-2-hydroxymethyl-15-methyl-$PGF_{2\alpha}$" should read -- 2-Decarboxy-2-hydroxymethyl-15-methyl-16,16-difluoro-$PGF_{2\alpha}$--.

Signed and Sealed this

Ninth Day of June 1981

[SEAL]

Attest:

RENE D. TEGTMEYER

Attesting Officer   Acting Commissioner of Patents and Trademarks